(12) United States Patent
Shoji et al.

(10) Patent No.: US 12,306,281 B2
(45) Date of Patent: May 20, 2025

(54) MAGNETIC RESONANCE IMAGING APPARATUS AND CONTROL METHOD THEREOF

(71) Applicant: FUJIFILM Healthcare Corporation, Kashiwa (JP)

(72) Inventors: Hiroki Shoji, Chiba (JP); Kosuke Ito, Chiba (JP); Hikaru Hanada, Chiba (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 18/433,931

(22) Filed: Feb. 6, 2024

(65) Prior Publication Data

US 2024/0264258 A1 Aug. 8, 2024

Related U.S. Application Data

(63) Continuation of application No. 17/877,017, filed on Jul. 29, 2022, now Pat. No. 11,927,658.

(30) Foreign Application Priority Data

Aug. 3, 2021 (JP) ................................. 2021-127670

(51) Int. Cl.
*G01V 3/00* (2006.01)
*G01R 33/48* (2006.01)
(Continued)

(52) U.S. Cl.
CPC ...... *G01R 33/5611* (2013.01); *G01R 33/4818* (2013.01); *A61B 5/055* (2013.01)

(58) Field of Classification Search
CPC .................. G01R 33/5611; G01R 33/4818
(Continued)

(56) References Cited

U.S. PATENT DOCUMENTS

2013/0251225 A1 9/2013 Liu et al.
2015/0157277 A1 6/2015 Goto et al.
(Continued)

FOREIGN PATENT DOCUMENTS

CN 105793722 B 7/2016
CN 107438398 A * 12/2017 ............... A61B 3/16
(Continued)

OTHER PUBLICATIONS

KR 20180068128 A (Park) (Year: 2018).*
(Continued)

*Primary Examiner* — Walter L Lindsay, Jr.
*Assistant Examiner* — Frederick Wenderoth
(74) *Attorney, Agent, or Firm* — Paul Teng

(57) ABSTRACT

Appropriate processing is executed in a method for excluding body motion data and image reconstruction according to a type and a characteristic of a body motion, so as to reduce an influence of the body motion, and prevent deterioration of image quality caused by exclusion of data generated during the body motion. An MRI apparatus includes a processing determination unit that collects k-space data and acquires body motion information from a sensor capable of detecting not only a respiratory motion but also general body motions, analyzes the body motion information obtained by the sensor, and branches and executes processing for subsequent data collection and image reconstruction according to the analysis result. The MRI apparatus determines, based on a temporal characteristic such as a duration and a frequency, and a spatial characteristic of the body motion, particularly a generation pattern in a k-space, body motion data to be excluded, and executes image reconstruction suitable for k-space data after exclusion of the body motion data.

14 Claims, 9 Drawing Sheets

(51) Int. Cl.
*G01R 33/561* (2006.01)
*A61B 5/055* (2006.01)

(58) Field of Classification Search
USPC .......................................................... 324/307
See application file for complete search history.

(56) References Cited

U.S. PATENT DOCUMENTS

| | | | | |
|---|---|---|---|---|
| 2015/0282890 | A1* | 10/2015 | Cohen | A61B 5/1128 600/424 |
| 2016/0256127 | A1 | 9/2016 | Lee et al. | |
| 2020/0110145 | A1 | 4/2020 | Zeller | |

FOREIGN PATENT DOCUMENTS

| | | | | |
|---|---|---|---|---|
| CN | 108627153 | A | | 10/2018 |
| CN | 110140042 | A | | 8/2019 |
| EP | 2158842 | A1 | | 3/2010 |
| JP | 2000287949 | A | * | 10/2000 |
| JP | 2008-067931 | A | | 3/2008 |
| JP | 2009-279238 | A | | 12/2009 |
| JP | 2017-505697 | A | | 2/2017 |
| JP | 2018-033691 | A | | 3/2018 |
| JP | 2018196661 | A | * | 12/2018 |
| JP | 2020-039869 | A | | 3/2020 |
| JP | 2020-130867 | A | | 8/2020 |
| JP | 2021-029777 | A | | 3/2021 |
| WO | WO2008/111416 | A1 | | 9/2008 |
| WO | WO2016/043010 | A1 | | 3/2016 |

OTHER PUBLICATIONS

Japanese official action dated Dec. 19, 2023 (and English translation thereof) in connection with Japanese Patent Application No. 2021-127670.

* cited by examiner

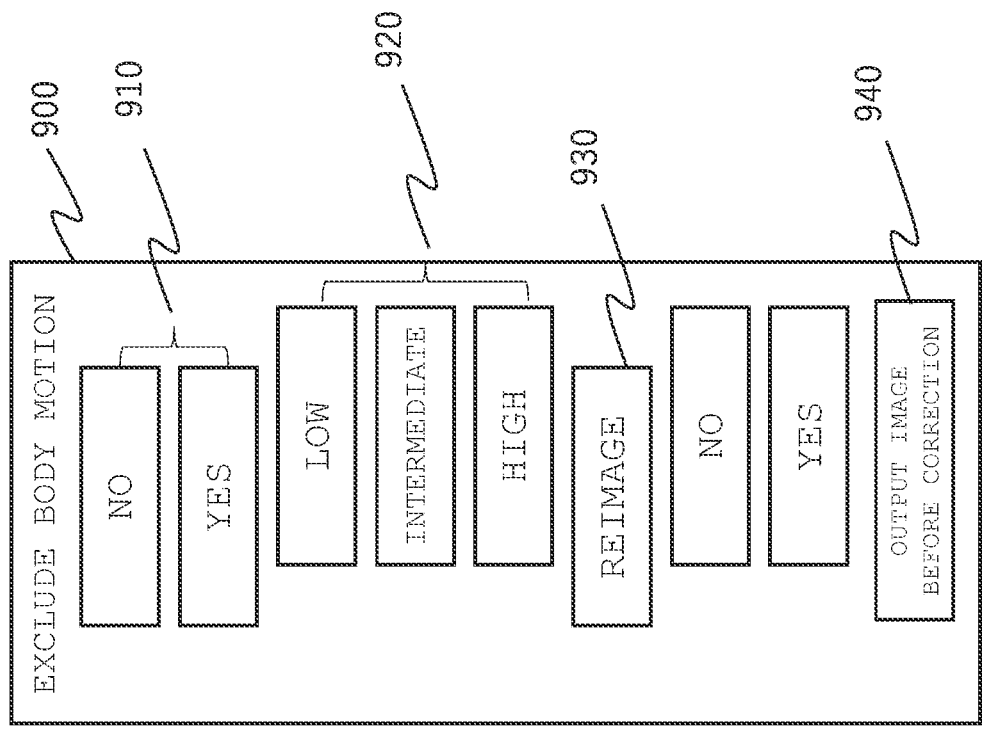

MAGNETIC RESONANCE IMAGING APPARATUS AND CONTROL METHOD THEREOF

CROSS-REFERENCE TO RELATED APPLICATIONS

This application is a Rule 1.53(b) continuation of application Ser. No. 17/877,017, filed Jul. 29, 2022, claiming the priority of Japanese Patent Application No. 2021-127670 filed with the Japan Patent Office on Aug. 3, 2021, the entire disclosure of which is hereby incorporated by reference herein.

BACKGROUND OF THE INVENTION

1. Field of the Invention

The present invention relates to a technique for coping with a body motion of a subject that occurs during imaging using a magnetic resonance imaging (MRI) apparatus.

2. Description of the Related Art

When a subject moves during an MRI examination, an influence of the movement is mixed into an echo signal and causes image quality deterioration. In order to solve this problem, various methods have been proposed in which, in MRI, a motion of a subject being examined is detected and an image is corrected by using a detection result (for example, US-A-2013-0251225). As one of the various methods, US-A-2013-0251225 discloses that a centric order is employed in which k-space data is collected from a low-frequency domain to a high-frequency domain, and high-frequency data is collected after collecting low-frequency data by breath-holding imaging; when a body motion detected by a sensor exceeds a threshold value during the data collection in the high-frequency domain, the k-space data measured during this period is excluded from data used for reconstruction; and an image is reconstructed by estimating missing parts due to the exclusion of the data by using a technique such as GRAPPA or compressed sensing, which are image reconstruction methods using parallel imaging, or by zero-filling the excluded data.

SUMMARY OF THE INVENTION

In the technique described in US-A-2013-0251225, data to be excluded is determined based on a magnitude of a respiratory motion targeted as the body motion to be detected. However, body motions other than respiration may cause image quality deterioration, and motions of the subject including these body motions other than respiration vary in a type, a motion time, a motion vector (a magnitude, a direction), and the like, and a sufficient correction cannot be made simply by excluding a body motion signal (a signal influenced by the body motion) based on the respiratory motion.

In MRI, an imaging method (for example, parallel imaging, or compressed sensing) for collecting data less than a measurement matrix required for image reconstruction is frequently used in order to execute high-speed imaging, and in such high-speed imaging, the image quality may be deteriorated due to a body motion correction depending on a relation in a k-space between non-measurement data determined according to an acceleration rate (reduction factor) and the data to be excluded by the body motion.

An object of the invention is to provide a technique capable of taking appropriate measures according to a type and a characteristic of a body motion, thereby reducing an influence of the body motion, and preventing deterioration of image quality caused by exclusion of data generated during the body motion.

The invention solves the above problem by using, as a sensor for detecting a body motion of a subject during an examination, a sensor capable of detecting not only a respiratory motion but also general body motions, analyzing body motion information obtained by such a sensor, and branching and executing processing for subsequent data collection and image reconstruction according to a temporal characteristic such as a duration and a frequency, and a spatial characteristic of the body motion, particularly a generation pattern in a k-space (measurement space).

That is, an MRI apparatus according to the invention includes: a measurement unit configured to measure a nuclear magnetic resonance signal of a subject; a calculation unit configured to generate an image by using the nuclear magnetic resonance signal measured by the measurement unit; a control unit configured to control operations of the measurement unit and the calculation unit; and a body motion analysis unit configured to receive, from a sensing unit disposed to be physically separated from the subject and configured to detect a body motion of the subject, a body motion detection result, and analyze a spatial characteristic and a temporal characteristic of the body motion. The control unit includes a processing determination unit configured to determine, by using body motion information obtained by the body motion analysis unit analyzing the body motion, a change in processing of at least one of the measurement unit and the calculation unit, and the control unit is configured to control the processing of the measurement unit and the calculation unit according to the determination result of the processing determination unit.

Since a correction method is selected according to a time pattern and/or an arrangement pattern in the k-space of body motion data, an insufficient correction or mixing of an artifact caused by a correction can be prevented, and an image in which an influence of the body motion is reduced can be obtained.

BRIEF DESCRIPTION OF THE DRAWINGS

FIG. 2A illustrates an MRI apparatus of a vertical magnetic field type, FIG. 2B illustrates an MRI apparatus of a horizontal magnetic field type, and FIG. 2C illustrates an MRI apparatus with enhanced spaciousness.

FIG. 9 is a diagram illustrating an example of a UI for user setting of body motion artifact removal.

DESCRIPTION OF THE PREFERRED EMBODIMENTS

First, an embodiment of an MRI apparatus to which the invention is applied will be described.

Outline of MRI Apparatus

Figure 1:
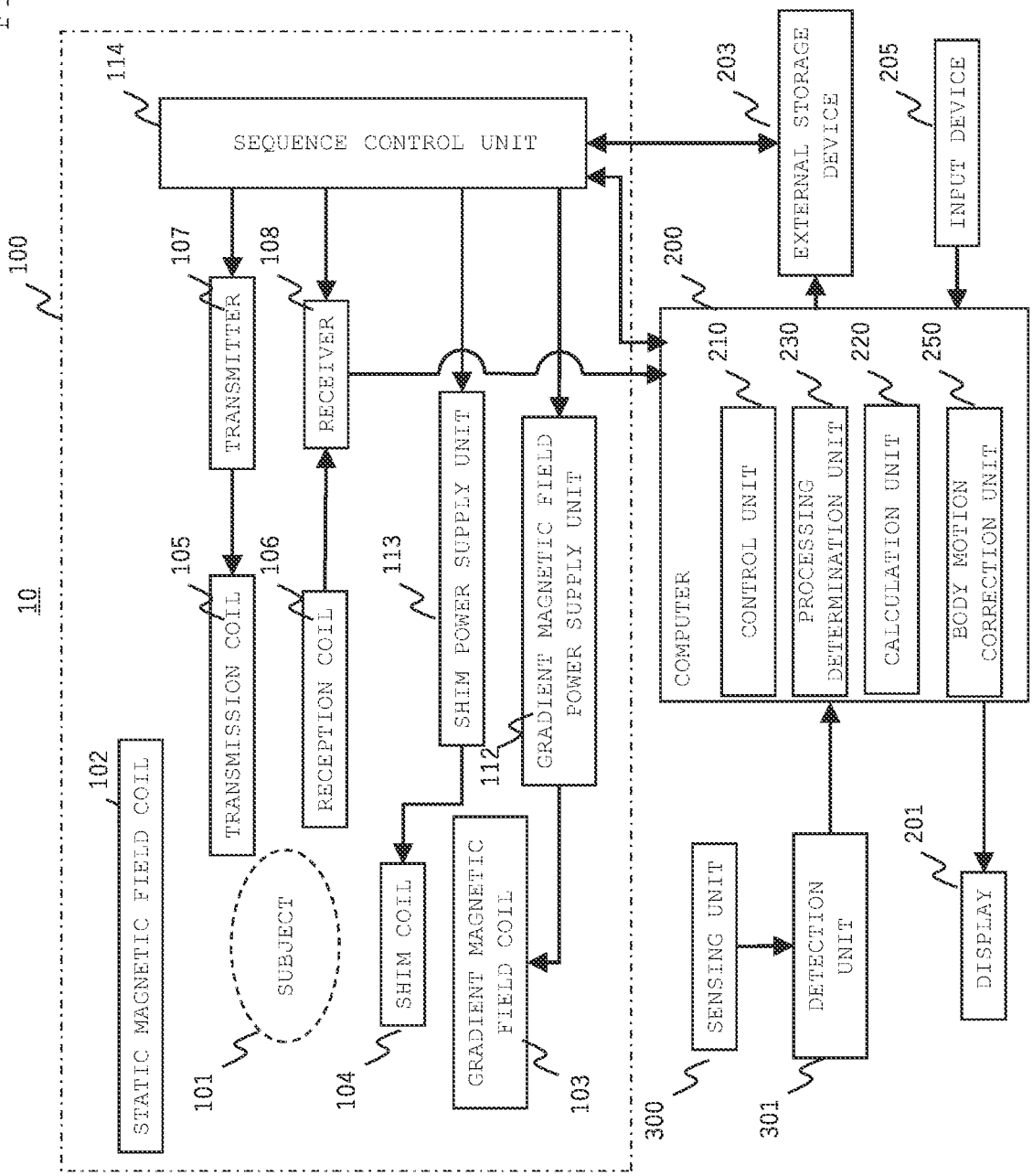
FIG. 1 is a block diagram illustrating a schematic configuration of an MRI apparatus according to an embodiment of the invention.

As illustrated in FIG. 1, an MRI apparatus 10 according to the present embodiment roughly includes a measurement unit 100 that measures a nuclear magnetic resonance signal generated from a subject 101, and a computer 200 that controls the measurement unit 100 and executes image reconstruction, corrections, and other calculations by using the nuclear magnetic resonance signal measured by the measurement unit 100.

The measurement unit 100 includes a static magnetic field coil 102 that generates a static magnetic field in a space in which the subject 101 is placed, a transmission unit (105, 107) that transmits a high-frequency magnetic field pulse to the subject 101 disposed in the static magnetic field, a reception unit (106, 108) that receives the nuclear magnetic resonance signal generated by the subject, and a gradient magnetic field coil 103 that applies a magnetic field gradient to the static magnetic field generated by the static magnetic field coil 102 in order to provide position information to the nuclear magnetic resonance signal.

Figure 2:
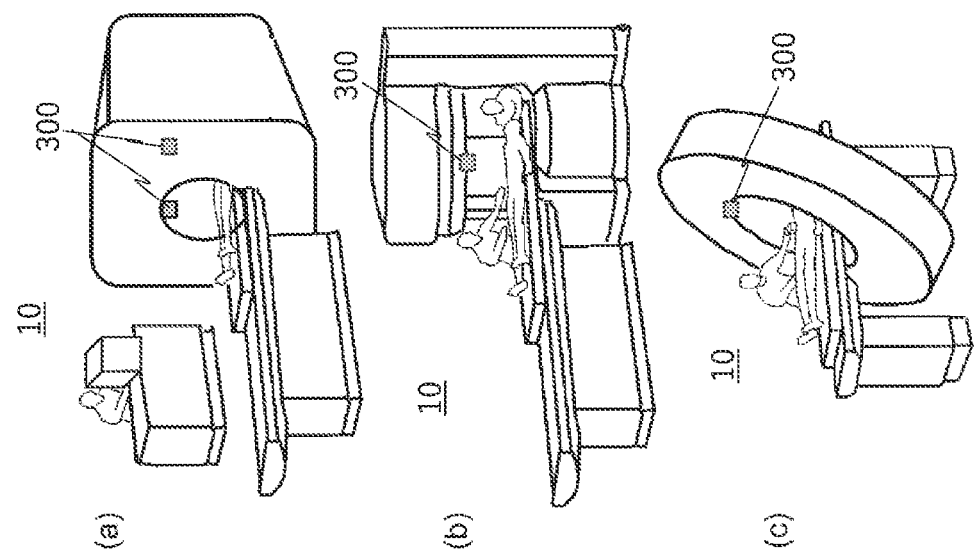
FIGS. 2A to 2C are external views of MRI apparatuses to which the invention is applied.

The static magnetic field coil 102 includes a normal conducting or superconducting static magnetic field coil, a static magnetic field generating magnet, and the like, is classified into a vertical magnetic field type, a horizontal magnetic field type, and the like depending on a direction of the generated static magnetic field, and a shape of the coil and an appearance of the entire apparatus are different depending on the type. FIGS. 2A to 2C illustrate appearances of MRI apparatuses that are different in these types. The present embodiment is applicable to any of the illustrated MRI apparatuses.

The transmission unit includes a transmission high-frequency coil 105 (hereinafter, simply referred to as a transmission coil) that transmits a high-frequency magnetic field to a measurement region of the subject 101, and a transmitter 107 including a high-frequency oscillator, an amplifier, and the like. The reception unit includes a reception high-frequency coil 106 (hereinafter, simply referred to as a reception coil) that receives the nuclear magnetic resonance signal generated from the subject 101, and a receiver 108 including a quadrature detection circuit, an A/D converter, and the like. The reception coil may be a multi-channel coil including a plurality of small reception coils, and in this case, the quadrature detection circuit and the A/D converter constituting the receiver 108 are connected to each of the small reception coils. The nuclear magnetic resonance signal received by the receiver 108 is transmitted to the computer 200 as a complex digital signal.

The gradient magnetic field coil 103 includes three sets of gradient magnetic field coils that respectively apply gradient magnetic fields in an x-direction, a y-direction, and a z-direction, and each set is connected to a gradient magnetic field power supply unit 112. The MRI apparatus may further include a shim coil 104 that adjusts a static magnetic field distribution and a shim power supply unit 113 that drives the shim coil 104. The position information can be provided to the nuclear magnetic resonance signal depending on a method for applying the gradient magnetic field.

The measurement unit 100 further includes a sequence control unit 114 that controls an operation of the measurement unit 100. The sequence control unit 114 controls operations of the gradient magnetic field power supply unit 112, the transmitter 107, and the receiver 108, and controls timings of applying the gradient magnetic field and the high-frequency magnetic field and receiving the nuclear magnetic resonance signal. A time chart of the control is referred to as a pulse sequence, is set in advance according to the measurement, and is stored in a storage device or the like provided in the computer 200.

The computer 200 controls operations of the entire MRI apparatus 10 and executes various calculation processing on the received nuclear magnetic resonance signal. Specifically, as illustrated in FIG. 3, the computer 200 includes a control unit 210 including a measurement control unit 211 that controls the measurement unit 100 via the sequence control unit 114, and a display control unit 212 that controls display of images and the like on a display; and a calculation unit 220 that executes a calculation such as image reconstruction (an image reconstruction unit 221).

The MRI apparatus according to the present embodiment further includes a processing determination unit 230 that changes or selects, according to a motion of the subject being imaged, a procedure or a method of processing executed in the MRI apparatus. Therefore, the computer 200 includes a body motion analysis unit 240 that receives a body motion signal from a body motion detection sensor (a sensing unit 300) to be described later and analyzes a body motion, and a body motion correction unit 250 that generates, based on an analysis result of the body motion, an image in which an influence of the body motion is reduced. The body motion analysis unit 240 includes a body motion data specifying unit 241 that determines data to be excluded (body motion data) from k-space data for image reconstruction. The body motion correction unit 250 generates a body motion-corrected image using k-space data after exclusion of the body motion data. The body motion correction unit 250 includes a k-space correction unit 252 that reconstructs a body motion-corrected image in the k-space, and an image space correction unit 253 that reconstructs a body motion-corrected image in an image space.

Figure 3:
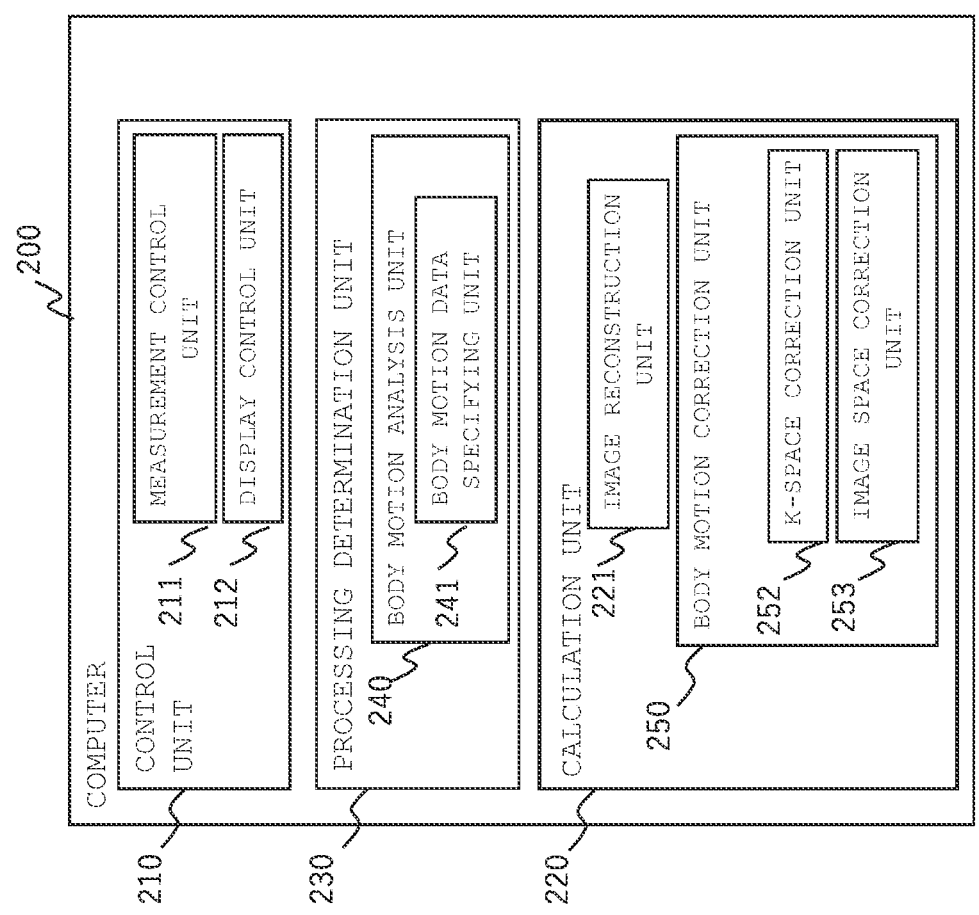
FIG. 3 is a functional block diagram of a computer according to the embodiment.

In FIG. 3, functions implemented in the computer 200 are illustrated as functions belonging to the control unit, the calculation unit, and the processing determination unit for convenience, whereas these functions may be independent of each other or overlap each other, and are not limited to FIG. 3. A part or all of functions of the body motion analysis unit 240 may be implemented by the sensing unit 300 independent of the MRI apparatus.

The sensing unit 300 includes an imaging unit such as a non-contact optical sensor, an infrared sensor, or a stereo camera, and a detection unit 301, and as illustrated in FIGS. 2A to 2C, the sensing unit 300 is disposed at a gantry of the MRI apparatus or a predetermined position in an examination room in which the MRI apparatus is placed, and images the subject being examined. The sensing unit 300 may be disposed at one or a plurality of places such as an entrance and an exit of the gantry, and an inside of the gantry, and the position where the sensing unit 300 is disposed and the number of sensing unit 300 may be appropriately changed according to a site to be imaged (a site to be examined) by the MRI apparatus.

The imaging of the sensing unit 300 may be appropriately started and ended by a user according to a start and end of the measurement of the MRI apparatus, or the control unit 210 may transmit a control signal so as to interlock the imaging of the sensing unit 300 with the measurement of the MRI apparatus.

The body motion analysis unit 240 analyzes a type, a motion time, a motion vector (a magnitude, a direction), and the like of the body motion based on a video of the subject imaged by the imaging unit of the sensing unit 300. The analysis can be executed by using an analysis algorithm known in the field of computer vision such as an optical flow, Remote Photoplethysmography (RPPG), Stereo Matching, and Pose Estimation. When the sensing unit 300 includes the body motion analysis unit 240, the sensing unit 300 transmits data, which is the analysis result, to the storage device or the like provided in the computer 200, and the processing determination unit 230 or the like reads the data from the storage device.

The body motion data specifying unit 241 specifies the data to be excluded (the body motion data) from the measured k-space data by using the analysis result of the body motion analysis unit 240.

The processing determination unit 230 performs a control of transmitting, based on the analysis result of the body motion analysis unit 240 and a result of the data to be excluded specified by the body motion data specifying unit 241, to each unit an instruction to change a measurement control procedure in the measurement control unit 211 and select a reconstruction method (a body motion correction method) in the calculation unit 220, and executing processing for reducing the influence of the body motion. When there is a user designation related to body motion prevention processing, the control is executed in consideration of the user designation.

The computer 200 includes a CPU, a memory, a storage device, and the like for implementing the functions described above, and is further connected with a display 201, an external storage device 203, an input device 205, and the like.

The display 201 and the input device 205 function as interface units (UI units) for the user, and the display 201 displays a result or the like obtained by the calculation processing to the user under the control of the display control unit 212. The input device 205 is a device for the user to input conditions, measurement parameters, and the like necessary for the measurement and the calculation processing. The external storage device 203 stores data used for various calculation processing executed by the computer 200, data obtained by the calculation processing, input conditions and parameters, and the like together with the storage device inside the computer 200.

The functions of these units of the computer 200 can be implemented as software embedded in the computer 200, and are implemented by the CPU loading a program (the software) stored by the storage device into the memory and executing the program. Various types of data used for processing of the functions and various types of data generated during the processing are stored in the storage device or the external storage device 203. At least one of the various functions implemented by the computer 200 may be implemented by an information processing apparatus that is independent of the MRI apparatus 10 and capable of transmitting and receiving data to and from the MRI apparatus 10. All or a part of the functions may be implemented by hardware such as an application specific integrated circuit (ASIC) and a field programmable gate array (FPGA) instead of the software.

Figure 4:
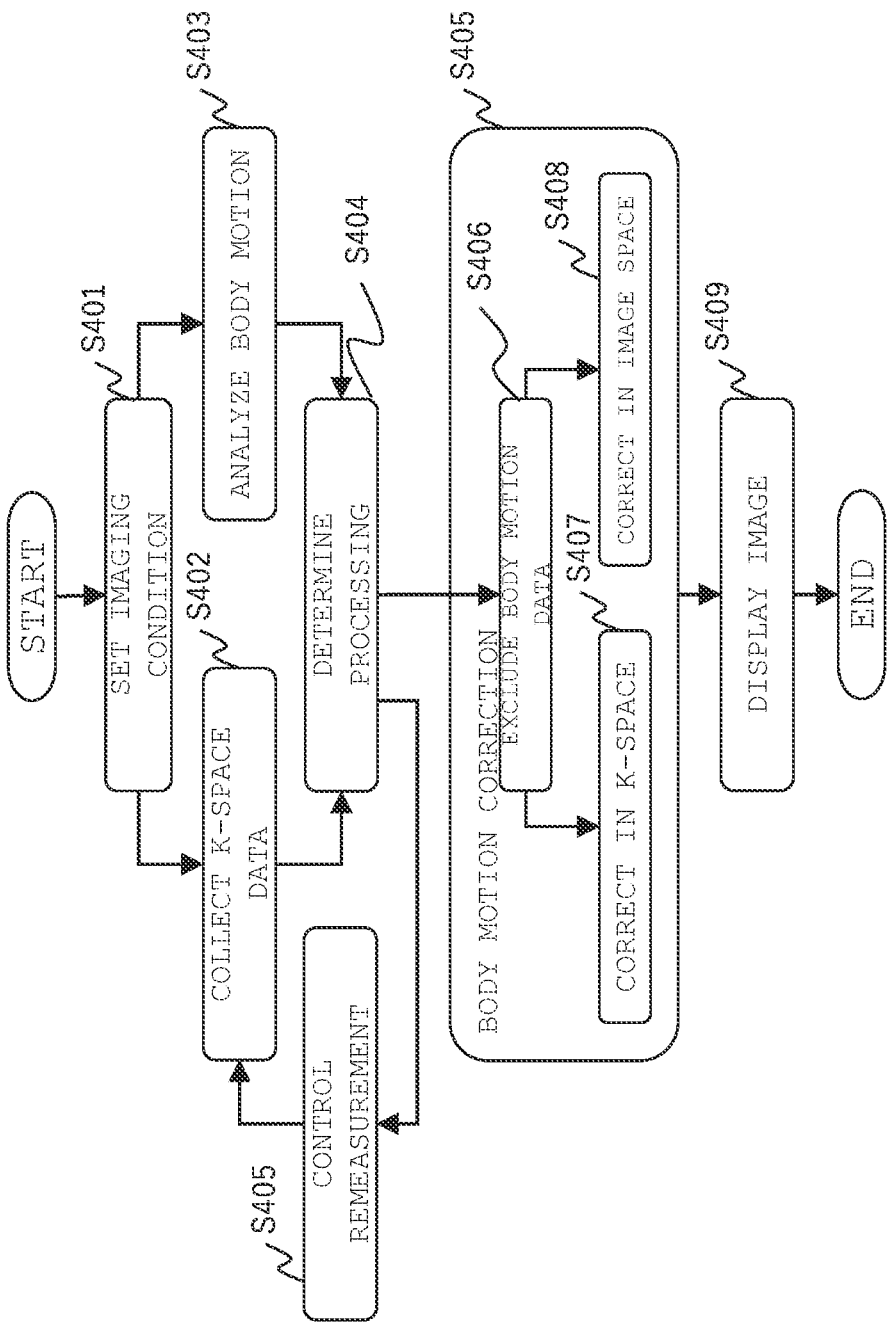
FIG. 4 is a diagram illustrating an outline of processing performed by the computer according to the embodiment.

Next, the operation of the computer 200 of the MRI apparatus 10 according to the present embodiment will be mainly described. FIG. 4 illustrates a flow of the operation.

First, setting of an imaging sequence and an imaging condition from the user is accepted via the input device 205 (S401). The imaging sequence is not particularly limited, but in order to shorten an imaging time, imaging methods that measure spatially overlapping signals, such as parallel imaging (PI) and simultaneous multi-slice (SMS) imaging may be selected and set. The imaging condition includes parameters (a repetition time TR and an echo time TE) of the imaging sequence, and includes a reduction factor (thinning-out rate) when an under-sampling (thinning-out measurement) (PI) in the k-space is executed. In the case of the simultaneous multi-slice excitation (SMS), setting of the number of slices is included. When the imaging condition and the like are set as an examination protocol, the condition and the like set in the examination protocol are read.

Further, in step S401, a user designation such as necessity or degree of the body motion correction may be accepted. In this case, the display control unit 212 displays a GUI for accepting the user designation on the display 201. The user determines conditions according to which one of (i) shortening of the imaging time and a calculation time and (ii) improving the accuracy of the body motion correction is to be prioritized and sets the determined conditions in the control unit 210 (the measurement control unit 211) and the processing determination unit 230, via the GUI.

The measurement control unit 211 operates the sequence control unit 114 according to the pulse sequence set based on the parameters input by the user, and measures the nuclear magnetic resonance signal (an echo signal) under a predetermined condition. The sequence control unit 114 controls each unit of the MRI apparatus 10 according to an instruction from the measurement control unit 211 to collect the k-space data for a collection matrix based on the parameters (S402). A collection order (ordering) and an under-sampling (thinning-out) method of the k-space data are determined by the pulse sequence calculated by the sequence control unit 114.

At the same time as the start of the measurement of the MRI apparatus, the sensing unit 300 images the subject being examined and detects the body motion. The body motion analysis unit 240 analyzes the type, the motion time, the motion vector (the magnitude, the direction), and the like of the body motion by using a technique such as the optical flow (S403). The type of the body motion includes a periodic motion such as a respiratory motion or a pulsation, a sudden motion such as coughing and sneezing, an irreversible position change such as a change in direction due to some reason, or the like, and can be determined based on the motion time (a frequency, a duration) and the motion vector.

The body motion data specifying unit 241 specifies, based on the time and the magnitude of the body motion analyzed by the body motion analysis unit 240, as body motion data to be excluded from the data being measured, data serving as an important cause of image quality deterioration when the body motion is present during the acquisition and being used as it is.

The processing determination unit 230 determines, based on the collected k-space data (S402) and information obtained by the body motion analysis (S403), whether to execute reimaging or the body motion correction. When it is determined to execute the body motion correction, whether to execute the body motion correction in the k-space or in the image space is also determined (S404).

When the imaging is executed at a predetermined reduction factor of such as PI or SMS imaging, it is determined whether a reduction factor obtained by summing up the thinning-out amount of PI or SMS imaging and a thinning-out amount when the body motion data is excluded is a ratio at which restoration of the image can be guaranteed in reconstruction processing, the body motion data is adjusted such that the ratio can guarantee the restoration, and finally, the body motion data to be excluded is determined (S406). For example, when the total reduction factor is too large for restoration (that is, when the data to be excluded is too much), the adjustment of the body motion data is executed by not excluding, from among the body motion data, body motion data having relatively less influence on the image quality and body motion data serving as the high-frequency data in the k-space.

The determination as to whether the reconstruction is possible is executed based on, for example, a preset upper limit of the reduction factor at which the restoration is possible. As will be described later, when a designation of a priority of the body motion correction or the like from the user is accepted via the display 201, the adjustment may be executed based on the user designation.

The calculation unit 220 (the body motion correction unit 250) reconstructs the data, which is obtained after the body motion data is excluded, in the k-space or the image space according to the determination of the processing determination unit 230, and generates a body motion-corrected reconstruction image (S407, S408).

The body motion-corrected reconstruction image is stored in the external storage device 203 or displayed on the display 201 by the display control unit 212 as necessary (S409). Data (raw data) before exclusion of the body motion data can also be stored in the external storage device 203, and accordingly, an image when no body motion correction is executed can be reconstructed and presented to the user as necessary.

These series of processing branches and body motion analysis results may be recorded as information to be added to an image finally obtained. In particular, an important reconstruction processing method influencing the image quality is preferably added to a series name indicating the processing branch and provided to the user. Such information may be presented to the user together with the image, or may allow the user to check a processing content afterward.

According to the present embodiment, appropriate processing can be selected and executed according to characteristics of various motions as well as the respiratory motion by monitoring an overall motion of the subject and determining, based on the information, the body motion data to be excluded.

Next, specific embodiments of the processing determination (FIG. 4: S404) executed by the processing determination unit 230 will be described based on an outline of the operation of the MRI apparatus described above. In the following embodiments, the flow illustrated in FIG. 4 is referred to as necessary.

First Embodiment

In the present embodiment, the processing determination unit 230 determines necessity of remeasurement of the measurement unit 100 in consideration of a position and an amount of the body motion data specified by the body motion data specifying unit 241, and determines processing of the body motion correction unit 250 when the remeasurement is not necessary. Hereinafter, the processing of the processing determination unit 230 (FIG. 4: S404) will be described with reference to a flow illustrated FIG. 5.

When k-space data and the body motion analysis result are input as premises (S4041), the body motion data specifying unit 241 compares each acquisition time of the measured k-space data with body motion information (a time and a magnitude of the body motion), and specifies data acquired when the body motion exceeds a predetermined magnitude as body motion data (S4042).

The processing determination unit 230 first determines the necessity of the remeasurement based on an amount of the specified body motion data and a position and interval of the body motion data in a k-space. For example, it is determined whether image reconstruction (image restoration) performed by the image reconstruction unit 221 is possible with remaining data after the body motion data is excluded from the k-space data used for the image reconstruction. At this time, when the k-space data is collected by imaging with a predetermined reduction factor, it is determined whether the image reconstruction is possible at a reduction factor obtained by summing up the thinning-out amount to and a thinning-out amount due to body motion data exclusion (S4043, S4044). A reduction factor at which the image reconstruction is possible can be set in advance based on an image reconstruction algorithm or the like implemented in the calculation unit 220.

When it is determined whether the image reconstruction is possible (S4044), an amount of the body motion data that can be excluded is determined based on the allowable reduction factor (the reduction factor set in advance), and when the amount of body motion data specified in S4042 is slightly larger than the determined amount, an adjustment may be executed so as to use the body motion data as data for image reconstruction, instead of being excluded, based on the magnitude of the body motion when the body motion data is acquired, the position of the body motion data in the k-space, or the like. That is, after adjustments such as not excluding data in which the body motion is relatively small or not excluding data in a low-frequency domain of the k-space are executed, only the determined amount of body motion data is excluded.

Figure 6:
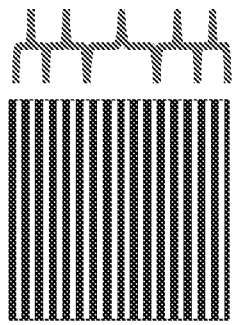
FIG. 6 is a diagram illustrating an example of the processing according to the first embodiment.

At this time, a limit on the data that can be excluded can also be set for each domain of the k-space. For example, as illustrated in FIG. 6, the k-space may be divided into domains such as a low-frequency domain, an intermediate-frequency domain, and a high-frequency domain, and data to be excluded may be limited for each domain. In the example illustrated in FIG. 6, high-frequency data can be excluded with a limit up to two adjacent lines, intermediate-frequency data can be excluded with a limit up to one adjacent line, and low-frequency data cannot be excluded.

In S4044, when it is determined that the image reconstruction is not possible, a command is transmitted to the measurement control unit 211 so as to remeasure the k-space data corresponding to the body motion data (S405). The remeasurement may be executed after all measurements are completed, or may be executed sequentially.

When the remeasurement is executed, the same processing determination is executed for the entire k-space data including the remeasured data.

When the body motion correction is to be executed without remeasurement, after the body motion data specified in S4042 or determined after the adjustment is excluded (S406), whether to execute the body motion correction by the k-space correction unit 252 or by the image space correction unit 253 is determined based on arrangements in the k-space of the body motion data to be excluded and other data (S4045). For example, in a case where no data (echo signal) is present in the vicinity of the body motion data when the body motion data is excluded in the k-space, the body motion correction is executed by the image space correction unit 253, and an image is generated by an PI calculation such as a SENSE method including compressed sensing and an iterative calculation (S408). In a case where data is present in the vicinity of the body motion data even when the body motion data is excluded in the k-space, a correction in the k-space is executed by using a technique (such as GRAPPA) for estimating missing data (excluded data and non-measurement data) in the k-space, and then an image is reconstructed by a normal image reconstruction method (S407).

A body motion correction method (a reconstruction method) by which an image with higher image quality can be obtained can be selected by differentiating the image reconstruction method based on the arrangement in the k-space of the body motion data to be excluded in this way.

When the k-space data before exclusion of the body motion data is data measured at a predetermined reduction factor, the processing in the image space or in the k-space may be performed in a one-time manner by executing the body motion correction, and may also be performed in a stepwise manner by executing the image reconstruction based on the normal PI calculation or the like and the image reconstruction after exclusion of the body motion data. For example, when the body motion correction is executed in the k-space, after the k-space data is obtained by estimating the non-measurement data with respect to the k-space data before exclusion of the body motion data, the body motion data is excluded, and the image reconstruction involving the body motion correction in the k-space or in the image space is executed on the k-space data after exclusion of the body motion data. Whether the body motion correction in the image reconstruction is executed in the k-space or in the image space can be determined based on the same reference as described above. When the body motion correction is executed in the image space, respective images may be independently reconstructed based on the SENSE method or the like using the k-space data before exclusion of the body motion data and the k-space data after exclusion of the body motion data to acquire a pair of images, and an image may be obtained by executing a calculation between these images (for example, synthesizes the images).

The image thus obtained is displayed on the display 201 together with a processing content (the image reconstruction method), which is additional information of the image, so as to be presented to the user (S409) as necessary, which is the same as the processing illustrated in FIG. 4.

According to the present embodiment, the body motion correction in which degradation of the image is prevented can be executed by determining whether the image reconstruction is possible in consideration of the reduction factor of the entire k-space data. A body motion-corrected image with high image quality can be obtained by selecting the image reconstruction method involving the body motion correction according to an arrangement of the k-space data after exclusion of the body motion data.

Second Embodiment

In the first embodiment, the processing determination unit determines whether to execute the remeasurement in consideration of the total of the reduction factor when the body motion data is excluded and the reduction factor set as the imaging condition, but in the present embodiment, the processing is differentiated depending on whether body motion data to be excluded is low-frequency data or high-frequency data in a k-space.

Figure 5:
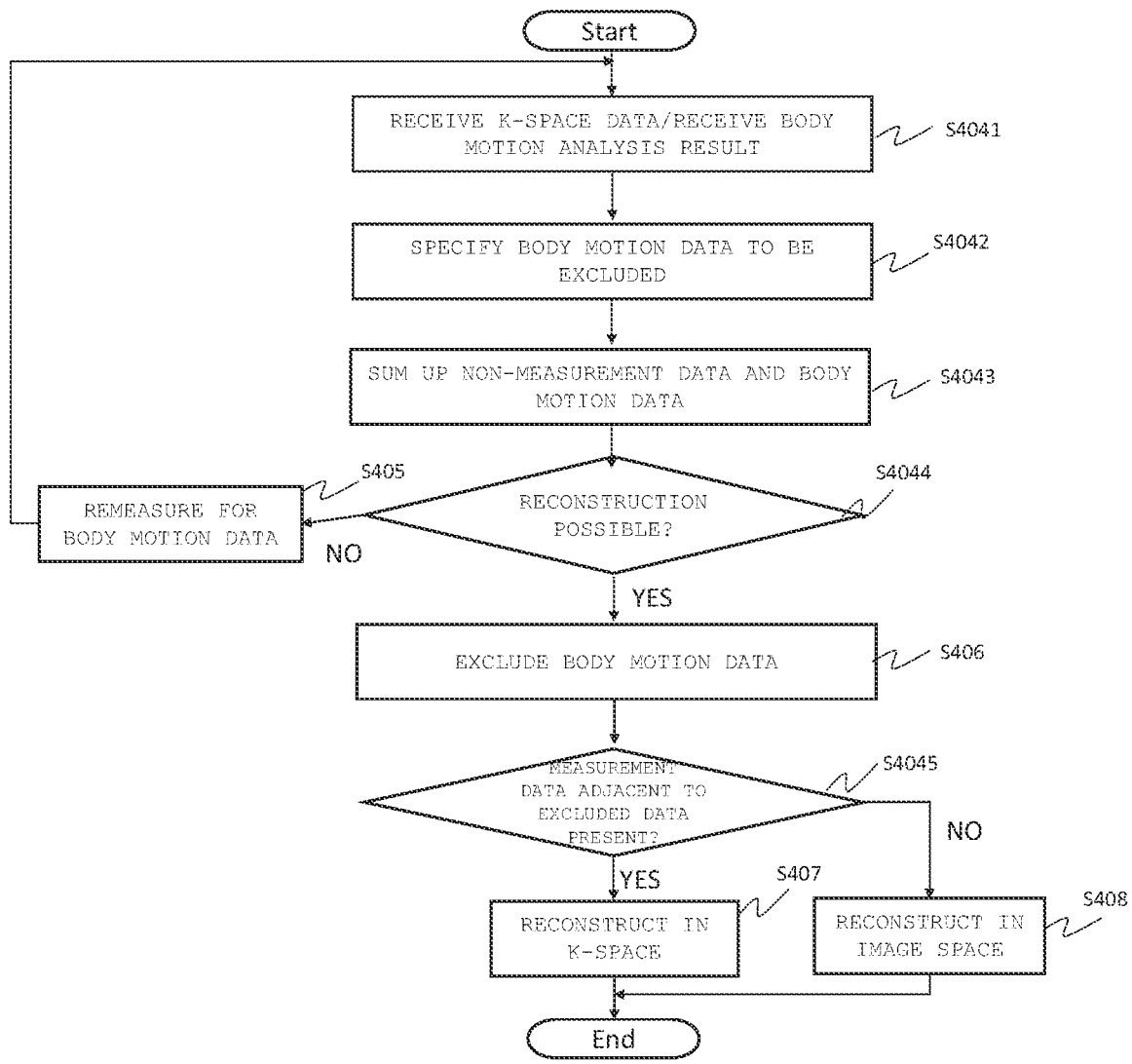
FIG. 5 is a diagram illustrating a flow of processing according to a first embodiment.
Figure 7:
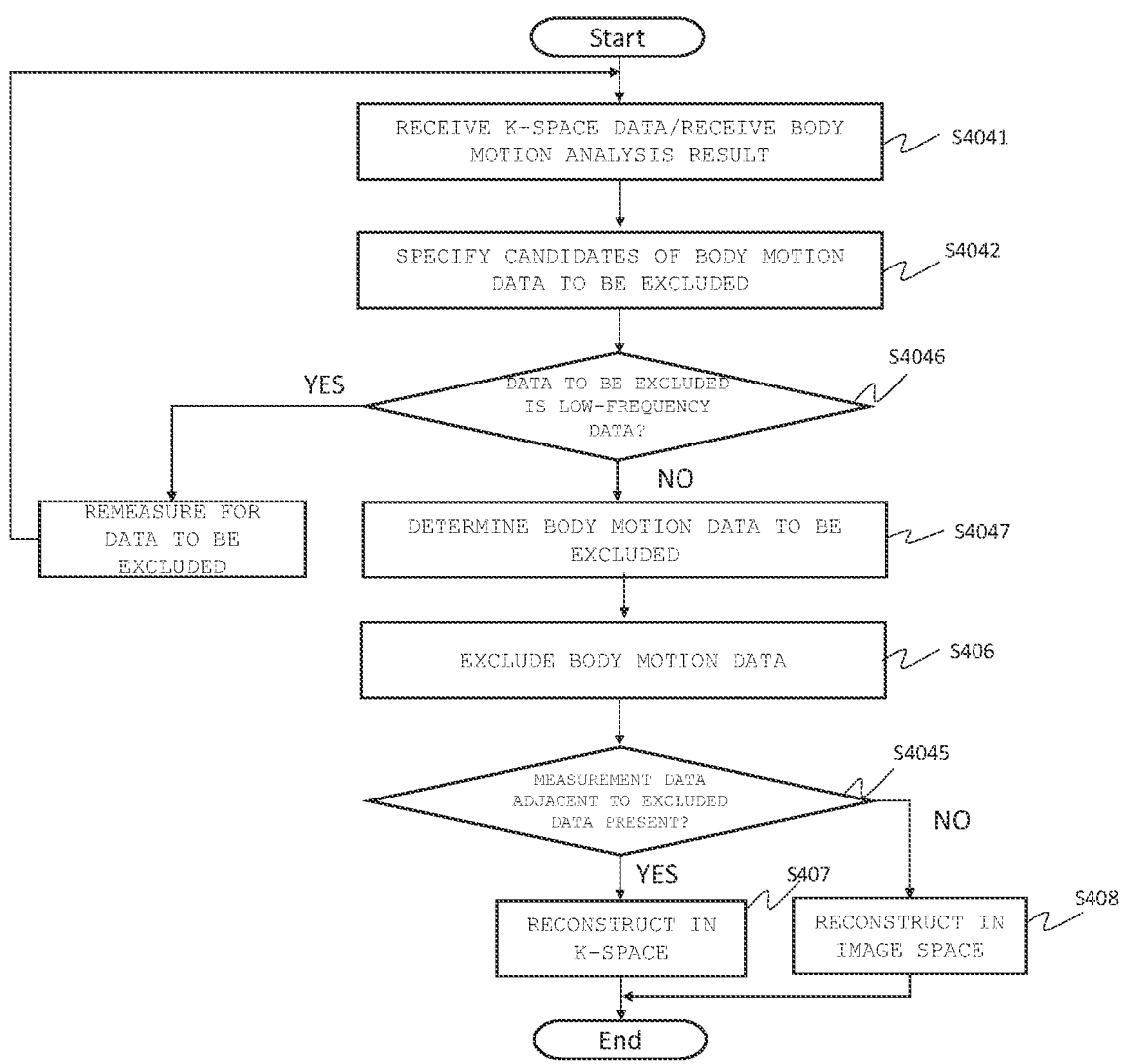
FIG. 7 is a diagram illustrating a flow of processing according to a second embodiment.

Hereinafter, processing of the processing determination unit 230 according to the present embodiment will be described with reference to a flow illustrated in FIG. 7. In FIG. 7, processing of the same contents as that in FIG. 5 is denoted by the same reference numeral, and a redundant description thereof will be omitted.

As well in the present embodiment, after k-space data and a body motion analysis result are input (S4041), the k-space data and the body motion are associated with each other, and the data collected when there is a motion is specified as the body motion data to be excluded (S4042).

Next, the processing determination unit 230 determines whether the specified body motion data is the low-frequency data (data in the vicinity of 0 encoding) or the high-frequency data in the k-space (S4046), and when the specified body motion data is the low-frequency data, the processing determination unit 230 transmits a command to the measurement control unit 211 to execute the remeasurement (S405). That is, S4041, S4042, and S4046 are repeated until the low-frequency data is collected.

Meanwhile, when the specified body motion data is the high-frequency data, whether to exclude the body motion data is determined according to a magnitude of the motion at the time of acquisition (S4047). A threshold value is set in advance for the magnitude of the motion, and when the magnitude exceeds the threshold value, the body motion data is excluded, and when the magnitude is equal to or less than the threshold value, the body motion data is not excluded. At this time, as in the first embodiment, a rule for data that can be excluded can also be set for each domain of the k-space. That is, as illustrated in FIG. 6, the number of lines that can be excluded is determined in advance for the intermediate-frequency domain and the high-frequency domain of the k-space, and the body motion data is excluded up to the number set in descending order of the magnitude of the motion.

Thereafter, as in the first embodiment, the determined body motion data is excluded (S406), and an image in which body motion correction is executed in the k-space or an image space is reconstructed according to a k-space data pattern after exclusion of the body motion data.

As well in the present embodiment, when the k-space data before exclusion of the body motion data is data measured at a predetermined reduction factor, for example, data measured by a PI method or an SMS method, the processing in the image space or in the k-space may be performed in a one-time manner by executing the body motion correction, or may be performed in a stepwise manner. For example, when the processing in the image space or in the k-space is performed in a stepwise manner, first, a data estimation calculation using GRAPPA or the like is executed on the k-space data before exclusion of the body motion data, after the estimation processing for the k-space data is executed, the body motion data is excluded from the k-space data, and the body motion correction is executed on the k-space data after exclusion of the body motion data. Whether the body motion correction is executed in the image space or in the k-space can be determined in the same manner as the determination in S4045.

In addition, when the processing in the image space or in the k-space is performed in a one-time manner, as in the first embodiment, whether image reconstruction is possible is determined based on a reduction factor determined based on the total of a thinning-out amount of data measured at a predetermined reduction factor and an amount (a thinning-out amount) of body motion data to be excluded, and if possible, the process proceeds to S407 or S408 to execute the body motion correction. Alternatively, the body motion correction may be executed after adjusting a thinning-out amount of data in the high-frequency domain among the body motion data to be excluded to obtain a reduction factor at which the image reconstruction is possible.

As a modification, it is also possible to execute a processing determination in which the first embodiment and the second embodiment are combined. That is, the initial processing determination may include not only the determination executed in S4043 and S4044 of the first embodiment based on the overall reduction factor, but also the determination in consideration of the position in the k-space of the body motion data to be excluded.

For example, the k-space is divided into a low-frequency domain and a high-frequency domain, a lower limit threshold value of the reduction factor is set for each of the low-frequency domain and the high-frequency domain, and when the low-frequency data is equal to or less than the lower limit of the reduction factor, the remeasurement is executed even if the overall reduction factor is determined to be a reduction factor at which the image reconstruction is possible, or when the body motion data to be excluded is almost high-frequency data, that is, when the reduction factor of the high-frequency domain is dominant in the overall reduction factor, the process proceeds to a body motion correction step without executing the remeasurement even if the overall reduction factor is determined to be a reduction factor at which the image reconstruction is impossible.

According to the present embodiment and the modification thereof, by determining subsequent processing based on the position in the k-space of the body motion data to be excluded, it is possible to guarantee information important for contrast in an image and to obtain the body motion-corrected image.

Third Embodiment

The present embodiment is also the same as other embodiments in that a motion of a subject is sensed by the non-contact sensing unit 300, the obtained body motion information is analyzed by the body motion analysis unit 240, and the processing determination unit 230 controls the measurement unit 100 and the body motion correction unit 250 based on the analysis result.

However, the first and second embodiments target processing corresponding to the body motion generated during main imaging, and in the present embodiment, processing in main imaging (a main scan) is determined based on body motion information obtained at the time of a pre-scan.

Figure 8:
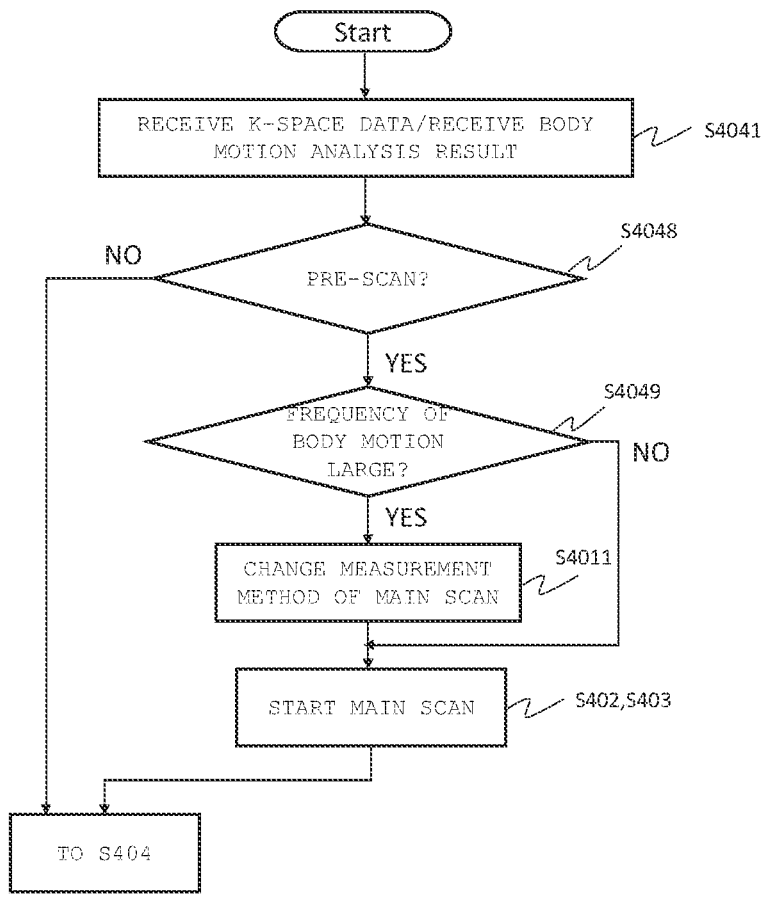
FIG. 8 is a diagram illustrating a flow of processing according to a third embodiment.

Hereinafter, processing according to the present embodiment will be described with reference to FIG. 8. Here, it is assumed that in the main scan, a Cartesian scan is set to collect k-space data in parallel in an axial direction.

When a measurement is started, k-space data collection is executed by the measurement unit 100 (FIG. 4: S402), body motion analysis is executed by the body motion analysis unit 240 (FIG. 4: S403), the processing determination unit 230 receives the k-space data and body motion information (S4041), and when the measurement is the pre-scan (S4048), whether the body motion occurs at a high frequency is determined based on the body motion information (S4049). The frequency of the body motion is determined, for example, by counting, at a predetermined time interval, the occurrence number of body motions with a magnitude of equal to or greater than a predetermined threshold value. The threshold value of the magnitude of the body motion and a threshold value of the occurrence number of body motions in a predetermined time are set in advance.

When the frequency of the body motion is low, the body motion can be corrected with relatively high accuracy by the methods according to the first and second embodiments, so that the main imaging (the main scan) following the pre-scan is executed under initially set imaging conditions (S401), and a processing determination is executed according to a flow as illustrated in FIG. 5 or 7.

Meanwhile, when the frequency of the body motion is determined to be high, a scan method of the main scan is switched from the Cartesian scan to a radial scan (a non-Cartesian scan) which is robust against the body motion. The radial scan includes a scan method of collecting data by differentiating an angle of one data line in a k-space, a scan method (a PROPELLER method) of collecting data by rotating a blade including a plurality of data lines to which phase encoding is provided, and the like, and any one of the methods may be adopted.

Here, when the scan method is switched, parameters by which a resolution, SNR, and contrast determined by the initially set imaging conditions are maintained are used. Specifically, the resolution, the SNR, and the contrast can be adjusted by adjusting the number of blades, a width of the blade, an echo time (TE), and the like.

In the main scan in which the scan method is switched, the image reconstruction is executed by excluding the body motion data, but in the radial scan, since the data can be collected at a relatively high density in a low-frequency domain of the k-space, it is preferable to execute the processing determination in consideration of the reduction factor after exclusion of the body motion data by the method according to the first embodiment.

For example, as illustrated in FIG. 5, after the body motion data to be excluded is specified based on the body motion analysis result for the k-space data (S4042), whether the reconstruction is possible with the k-space data after exclusion of the body motion data (the k-space data after the body motion data is excluded from undersampled k-space data when the data is collected at a predetermined reduction factor) is determined (S4044), and if the reconstruction is possible, the body motion data is excluded to reconstruct the image.

When the image reconstruction is executed, for example, by the PROPELLER method, whether an echo signal is present in the vicinity of the excluded body motion data is determined for each blade (S4045), whether to execute the body motion correction in an image space or the body motion correction in the k-space is determined based on the determination result, the image reconstruction is executed, and an image in which aliasing is unfolded for each blade is obtained (S407, S408). In the case of the correction in the image space, an image for each blade in which the aliasing is unfolded is subjected to inverse Fourier transform and rearranged in the k-space, the radially arranged data is rearranged (gridded) on orthogonal coordinates, and Fourier transform is executed again to reconstruct the image. In the case of the correction in the k-space, after data for each blade is gridded in the k-space, missing data is estimated, and the Fourier transform is executed to reconstruct the image.

According to the present embodiment, since a generation pattern of the body motion data in the k-space data is predicted based on the body motion information acquired at the time of the pre-scan, and the scan method of the main scan is determined according to the prediction, the main scan that is less likely to be influenced by the body motion can be executed even if the body motion occurs at a relatively high frequency.

Fourth Embodiment

The present embodiment is an embodiment related to a function of the display control unit 212, and is characterized in that a user designation is accepted for a body motion correction, and processing executed by the processing determination unit 230 is changed according to the user designation.

In the first to third embodiments described above, the threshold values of such as the magnitude and the frequency of the body motion used by the processing determination unit 230 in the body motion information determination are set to predetermined values in advance, whereas in the present embodiment, the user selects necessity of the body motion correction and the degree of processing, and thus the user's preference is reflected in the processing determination such as changing the threshold values.

An example of a GUI 900 for accepting the user designation is illustrated in FIG. 9. In the illustrated example, the GUI 900 includes a block 910 for accepting user's selection about the necessity of processing for excluding the body motion, a block 920 for accepting user's designation of a degree of the processing when the body motion correction is executed, a block 930 for accepting user's selection about the necessity of reimaging to remeasure the body motion data, and a block 940 for outputting an image reconstructed with data before the correction.

Depending on the user or a purpose or situation of an examination, short-time imaging may be required rather than the body motion correction. In such a case, the user can select "NO" for the body motion correction or select "NO" for reimaging even if the body motion correction is to be executed, and thus the user can execute imaging according to the preference and the situation.

When "YES" is selected for the body motion correction, for example, a threshold value used for determining body motion data to be excluded by the body motion data specifying unit 241 is changed according to which of "LOW", "INTERMEDIATE", and "HIGH" is selected, and if "LOW" is selected, the threshold value is increased, and only data with relatively large body motion is determined as the body motion data to be excluded. When the processing determination unit 230 adjusts the body motion data to be excluded, an amount of the body motion data to be excluded may be adjusted according to the degree of the body motion correction. For example, if "LOW" is selected, the amount of the body motion data to be excluded is reduced, and the image is reconstructed with more k-space data.

Further, an allowable range of the body motion data to be excluded may be determined according to the degree of the body motion correction. For example, when "HIGH" is selected for the body motion correction, the k-space data can be excluded with a limit up to two adjacent lines, and when "LOW" is selected for the body motion correction, the k-space data can be excluded with a limit up to one adjacent line. As illustrated in FIG. 6, different settings may be made for each domain, and a domain division in this case may be changed according to the user selection. At this time, an image as illustrated in FIG. 6 may be displayed as a GUI, and the user may determine a domain on the GUI and set a line interval that can be excluded for each domain.

When the block 940 "OUTPUT IMAGE BEFORE CORRECTION" of the GUI is selected, an image is reconstructed by using the k-space data (raw data) before exclusion of the body motion data, and is displayed on the display 201. By checking such an image, the user can check an effect of the body motion correction and information (for example, detailed information) that is likely to be lost due to the body motion correction, and can also execute, according to the checking result, a result of differentiating the degree of the body motion correction by using the raw data, for example, a result of changing the "HIGH" body motion correction to the "LOW" body motion correction, as post-processing, and output the result.

Although not illustrated in FIG. 9, a GUI not limited to FIG. 9 can be presented, such as displaying a GUI for selecting a body motion correction method (the method according to the first embodiment, the method according to the second embodiment, or a combination thereof), or displaying a GUI for accepting a user instruction regarding contents of the methods.

Although the embodiments of the invention have been described above, the invention is not limited to the imaging methods and the processing methods exemplified in the embodiments, and various changes can be made, for example, by combining the methods of the embodiments or omitting processing that is not important for the configuration of the invention within a technically consistent range.

What is claimed is:

1. A magnetic resonance imaging apparatus, comprising:
   a measurement unit configured to measure a nuclear magnetic resonance signal of a subject;
   a calculation unit configured to generate an image by using the nuclear magnetic resonance signal measured by the measurement unit;
   a control unit configured to control operations of the measurement unit and the calculation unit;
   a body motion analysis unit configured to analyze, based on a body motion detection result received from a sensing unit disposed to be physically separated from the subject, and configured to detect a body motion of the subject, a spatial characteristic and a temporal characteristic of the body motion; and
   a processing determination unit configured to determine, by using body motion information obtained by the body motion analysis unit, a change in processing of at least one of the measurement unit or the calculation unit, the control unit controlling the processing of the measurement unit and the calculation unit according to the determination result of the processing determination unit, wherein
   the processing determination unit is further configured to determine, by using the body motion information, at least one of a body motion correction or remeasurement to be carried out, and to acquire the body motion information from the body motion analysis unit during a pre-scan performed by the measurement unit, and control, based on the body motion information acquired in the pre-scan, an image pulse-sequence used in a main scan executed following the pre-scan.

2. A control method of a magnetic resonance imaging apparatus including a measurement unit configured to measure a nuclear magnetic resonance signal of a subject, and a calculation unit configured to execute a calculation by using the nuclear magnetic resonance signal, the control method comprising:
   an analysis step of analyzing, based on a body motion detection result received from a sensing unit disposed to be physically separated from the subject being imaged by the magnetic resonance imaging apparatus and detecting a body motion of the subject, a spatial characteristic and a temporal characteristic of the body motion;

a processing determination step of determining, by using body motion information obtained when analyzing in the analysis step, a change in processing of at least one of the measurement unit or the calculation unit;

a step of controlling the processing of the measurement unit and the calculation unit according to the determination result obtained in the processing determination step;

a step of determining, by using the body motion information, which of a body motion correction and remeasurement should be carried out; and a step of acquiring the body motion information during a pre-scan performed by the measurement unit, and controlling, based on the body motion information acquired in the pre-scan, an image pulse-sequence used in a main scan executed following the pre-scan.

3. The magnetic resonance imaging apparatus according to claim 1, wherein the body motion analysis unit is further configured to output the spatial characteristic and the temporal characteristic of the body motion as the body motion information, using a body motion analysis algorithm of a computer vision.

4. The magnetic resonance imaging apparatus according to claim 1, wherein the processing determination unit is further configured to determine, by using the body motion information, whether the body motion correction is necessary, and when determining that the body motion correction is necessary, the processing determination unit determines whether to execute body motion correction processing of the calculation unit in an image space or in a measurement space.

5. The magnetic resonance imaging apparatus according to claim 1, wherein the processing determination unit is further configured to specify, based on the body motion information, a nuclear magnetic resonance signal to be excluded from the nuclear magnetic resonance signal used by the calculation unit for image generation.

6. The magnetic resonance imaging apparatus according to claim 1, wherein the processing determination unit is further configured to, when a frequency of the body motion is high in the body motion information acquired during the pre-scan, change a measurement method for the main scan to a non-Cartesian measurement.

7. The magnetic resonance imaging apparatus according to claim 1, wherein the body motion analysis unit is further configured to analyze a type, a motion time, and a motion vector, each of the body motion, and the magnetic resonance imaging apparatus further comprises a body motion specifying unit configured to determine, based on the analysis result of the body motion analysis unit, data to be excluded from k-space data for image reconstruction.

8. The magnetic resonance imaging apparatus according to claim 5, wherein the processing determination unit is further configured to determine whether a reduction factor when the nuclear magnetic resonance signal to be excluded is excluded is a value at which image reconstruction by the calculation unit is possible, and specify the nuclear magnetic resonance signal to be excluded.

9. The magnetic resonance imaging apparatus according to claim 5, wherein the measurement unit is further configured to measure the nuclear magnetic resonance signal at a predetermined acceleration rate, the calculation unit is further configured to execute image reconstruction by using an under-sampled nuclear magnetic resonance signal, and the processing determination unit is further configured to determine whether a total reduction factor of a reduction factor when the nuclear magnetic resonance signal to be excluded is excluded and a reduction factor determined by the predetermined acceleration rate is a value at which the image reconstruction by the calculation unit is possible, and specify the nuclear magnetic resonance signal to be excluded.

10. The magnetic resonance imaging apparatus according to claim 5, wherein the processing determination unit is further configured to differentiate, depending on a domain of a measurement space, a rule for excluding the nuclear magnetic resonance signal.

11. The magnetic resonance imaging apparatus according to claim 5, wherein the processing determination unit is further configured to determine whether the nuclear magnetic resonance signal to be excluded is low-frequency data or high-frequency data in a measurement space, and determine necessity of remeasurement based on the determination result.

12. The magnetic resonance imaging apparatus according to claim 9, wherein the calculation unit is further configured to execute the image reconstruction with a total reduction factor of a reduction factor after the nuclear magnetic resonance signal to be excluded is excluded and the reduction factor determined by the predetermined acceleration rate.

13. The magnetic resonance imaging apparatus according to claim 9, wherein the calculation unit is further configured to independently execute the image reconstruction with the reduction factor determined by the predetermined acceleration rate and the image reconstruction with a reduction factor after the nuclear magnetic resonance signal to be excluded is excluded.

14. The magnetic resonance imaging apparatus according to claim 7, wherein the processing determination unit is further configured to perform a control of transmitting, based on the analysis result of the body motion analysis unit and based on the data to be excluded from the k-space data, to the measurement unit an instruction to change a measurement control procedure and to the calculation unit a selection of a reconstruction method to correct for the body motion.

* * * * *